(12) United States Patent
Ishii et al.

(10) Patent No.: US 7,766,828 B2
(45) Date of Patent: Aug. 3, 2010

(54) ESTIMATION APPARATUS AND ITS CONTROL METHOD

(75) Inventors: Mie Ishii, Tokyo (JP); Masakazu Matsugu, Yokohama (JP); Katsuhiko Mori, Kawasaki (JP); Yusuke Mitarai, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/665,862

(22) PCT Filed: Oct. 25, 2005

(86) PCT No.: PCT/JP2005/019941

§ 371 (c)(1),
(2), (4) Date: Apr. 20, 2007

(87) PCT Pub. No.: WO2006/046723

PCT Pub. Date: May 4, 2006

(65) Prior Publication Data

US 2007/0270664 A1 Nov. 22, 2007

(30) Foreign Application Priority Data

Oct. 27, 2004 (JP) .............................. 2004-312858

(51) Int. Cl.
*A61B 5/00* (2006.01)
(52) U.S. Cl. ...................... 600/300; 434/236; 434/238; 128/920
(58) Field of Classification Search ................. 600/300, 600/301; 128/903–905, 920
See application file for complete search history.

(56) References Cited

U.S. PATENT DOCUMENTS

| 6,148,243 | A | 11/2000 | Ishii et al. | |
|---|---|---|---|---|
| 6,607,484 | B2 | 8/2003 | Suzuki et al. | ................ 600/300 |
| 6,968,294 | B2 * | 11/2005 | Gutta et al. | .................. 702/188 |
| 2003/0218544 | A1 | 11/2003 | Shinada | ...................... 340/575 |
| 2007/0208678 | A1 | 9/2007 | Matsugu | |

FOREIGN PATENT DOCUMENTS

| JP | 5-12023 | 1/1993 |
|---|---|---|
| JP | 10-228295 | 8/1998 |
| JP | 2001-083984 | 3/2001 |
| JP | 2001-344352 | 12/2001 |
| JP | 2002-215183 | 7/2002 |
| JP | 2003-237588 | 8/2003 |

OTHER PUBLICATIONS

U.S. Appl. No. 11/597,061, International filing date Jun. 6, 2005, Kaneda, et al.

* cited by examiner

*Primary Examiner*—Henry M Johnson, III
*Assistant Examiner*—Kai Rajan
(74) *Attorney, Agent, or Firm*—Fitzpatrick, Cella, Harper & Scinto

(57) ABSTRACT

A condition analysis unit (1302) estimates a surrounding environment and psychological state of the user on the basis of image data, voice data, and living body information. When the estimated psychological state is a predetermined state, a cause estimation unit (1303) estimates based on the living body information whether or not the physical condition of the user is bad. When the estimated psychological state is the predetermined state, the cause estimation unit estimates a cause of the psychological state on the basis of the surrounding environment.

7 Claims, 12 Drawing Sheets

ESTIMATION APPARATUS AND ITS CONTROL METHOD

TECHNICAL FIELD

The present invention relates to a technique for estimating information that pertains to an emotion of the user.

BACKGROUND ART

Conventionally, it is demanded to realize an interface apparatus which recognizes the personality and emotion of a person and executes processing in accordance with the recognition result. In order to implement such human processing, it is indispensable to develop a personality recognition technique and emotion recognition technique required to recognize the personality and emotion of the user.

According to the conventional technique associated with emotion recognition, emotion recognition is made on the basis of voice information and image information (such as an expression, action, or the like) of the user (for example, Japanese Patent Laid-Open Nos. 5-12023, 10-228295, and 2001-83984). In patent reference 2 of them, an emotion recognition result obtained based on voice information and that obtained from image (expression) information are multiplied by predetermined weights and are combined, thus obtaining a final emotion recognition result.

In Japanese Patent Laid-Open No. 2001-83984, the personality is recognized in consideration of physical and action features of the user in addition to the voice and expression information, thus further improving the emotion recognition precision.

By the way, human emotions such as delight, anger, sorrow, and pleasure necessarily have causes that drive such emotions. For example, when a person is "angry", this emotion may have various causes.

The conventional interface apparatus applies the same control to the same emotion independently of the psychological state and physical condition of the user.

The present invention has been made in consideration of the above problems, and has as its object to provide a technique which estimates a cause that has driven the user to the current emotion, and communicates with the user in accordance with the estimated cause.

DISCLOSURE OF INVENTION

In order to achieve an object of the present invention, for example, an estimation apparatus of the present invention comprises the following arrangement.

That is, an estimation apparatus characterized by comprising:

image input means for inputting image data of a user;
voice input means for inputting voice data of the user;
living body information input means for inputting living body information of the user;
first estimation means for estimating a surrounding environment of the user on the basis of the image data, voice data, and living body information;
holding means for holding reference data serving as a reference used upon estimating a psychological state of the user;
second estimation means for estimating the psychological state of the user by comparing at least one of the image data, voice data, and living body information with the reference data; and
third estimation means for, when the psychological state of the user estimated by the second estimation means is a predetermined state, estimating a cause of the psychological state of the user on the basis of the surrounding environment estimated by the first estimation means.

In order to achieve an object of the present invention, for example, a method of controlling an estimation apparatus of the present invention comprises the following arrangement.

That is, a method of controlling an estimation apparatus, characterized by comprising:

an image input step of inputting image data of a user;
a voice input step of inputting voice data of the user;
a living body information input step of inputting living body information of the user;
a first estimation step of estimating a surrounding environment of the user on the basis of the image data, voice data, and living body information;
a holding step of holding reference data serving as a reference used upon estimating a psychological state of the user;
a second estimation step of estimating the psychological state of the user by comparing at least one of the image data, voice data, and living body information with the reference data; and
a third estimation step of estimating, when the psychological state of the user estimated in the second estimation step is a predetermined state, a cause of the psychological state of the user on the basis of the surrounding environment estimated in the first estimation step.

Other features and advantages of the present invention will be apparent from the following description taken in conjunction with the accompanying drawings, in which like reference characters designate the same or similar parts throughout the figures thereof.

BRIEF DESCRIPTION OF DRAWINGS

The accompanying drawings, which are incorporated in and constitute a part of the specification, illustrate embodiments of the invention and, together with the description, serve to explain the principles of the invention.

BEST MODE FOR CARRYING OUT THE INVENTION

Preferred embodiments of the present invention will now be described in detail in accordance with the accompanying drawings.

First Embodiment

Figure 1:
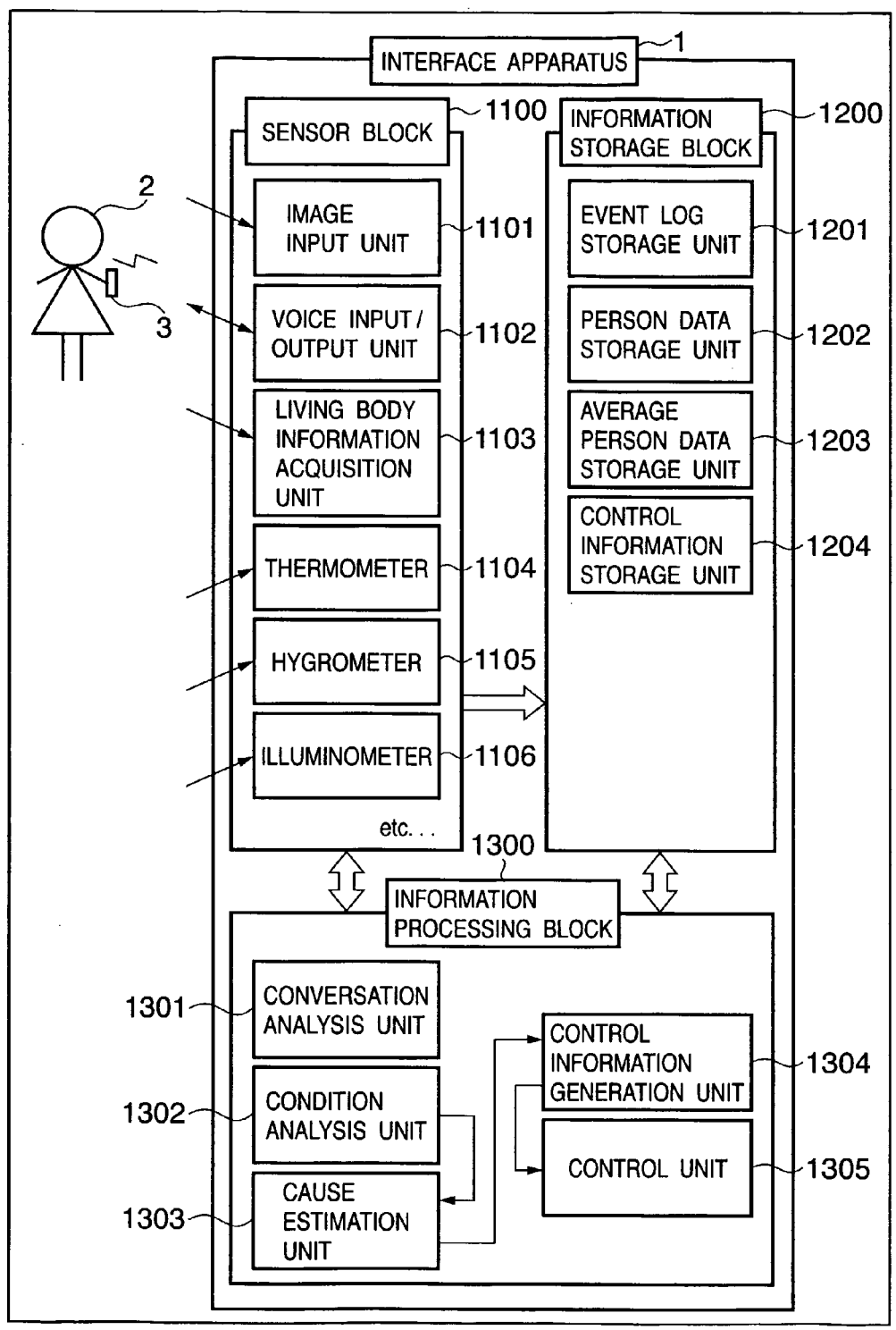
FIG. 1 is a block diagram showing the functional arrangement of a system including an estimation apparatus according to the first embodiment of the present invention.

FIG. 1 is a block diagram showing the functional arrangement of a system including an estimation apparatus (to be referred to as an interface apparatus hereinafter) according to this embodiment. In the following description, assume that units which form an interface apparatus 1 shown in FIG. 1 are configured by hardware components. However, some or all of these units may be implemented by software.

Referring to FIG. 1, reference numeral 2 denotes a user. In the following description, the interface apparatus estimates a cause that has driven the user 2 to the current emotion, and makes communication with the user 2 in accordance with the estimated result. Reference numeral 3 denotes a measuring instrument which measures living body information including the body temperature, heart rate, blood pressure, perspiration, and the like of the user, and transmits the measured living body information to the interface apparatus 1. The measuring instrument 3 is attached to the user 2, and this living body information is periodically measured and is transmitted to the interface apparatus 1 by radio.

Reference numeral 1 denotes an interface apparatus according to this embodiment, which is roughly configured by a sensor block 1100, information storage block 1200, and information processing block 1300.

The sensor block 1100 is roughly classified to units (image input unit 1101, voice input/output unit 1102, and living body information acquisition unit 1103) for acquiring image information, voice information, and living body information of an external world concerned with an user, and units (thermometer 1104, hygrometer 1105, and illuminometer 1106) for measuring information of the external world.

The image input unit 1101 captures a physical space as a moving image, and captures a surrounding environment including the user 2 in the following description. As a result, the surrounding environment of the user 2 and the expression and body action of the user 2 can be obtained as an image. The image input unit 1101 has a person tracking function of tracking a specific person as needed.

The voice input/output unit 1102 collects voice information on the physical space, and outputs a voice on the basis of a voice signal output from the information processing block 1300. In the following description, the voice input/output unit 1102 collects voice information from the surrounding environment including the user 2, and outputs a message to the user 2.

The living body information acquisition unit 1103 serves as an I/F unit for receiving the aforementioned living body information transmitted from the measuring instrument 3.

The thermometer 1104 measures the temperature of the external world of the interface apparatus 1. The hygrometer 1105 measures the humidity of the external world of the interface apparatus 1. The illuminometer 1106 measures the illuminance of the external world of the interface apparatus 1. In the following description, the temperature measured by the thermometer 1104, the humidity measured by the hygrometer 1105, and the illuminance measured by the illuminometer 1106 will be referred to as environment information together.

The information storage block 1200 stores various kinds of information obtained from the sensor block 1100, information to be stored in advance, and the like, and comprises an event log storage unit 1201, person data storage unit 1202, average person data storage unit 1203, and control information storage unit 1204.

The event log storage unit 1201 stores the living body information and environment information obtained from the sensor block 1100 as an event log together with the current date and time.

The person data storage unit 1202 stores personal data of the user 2 in advance. This personal data includes data required to specify the user 2, i.e., the face and whole body images of the user 2, feature amount data of a voice of the user 2, and the like. Also, this personal data includes physical information of the user 2 such as the body height, body weight, average body temperature, average pulse rate, and the like of the user 2.

The average person data storage unit 1203 stores feature amount data of voices, expressions, actions, heart rates, and the like for respective emotions of an average person.

For example, voice features include voice pitch, loudness, frequency characteristic, and the like, and are given as data having certain ranges in association with respective emotions of delight, anger, sorrow, and pleasure. Also, expression features include motions of eyes, mouth, eyebrows, and the like, and are given as having certain ranges in association with respective emotions.

The control information storage unit 1204 sequentially stores the processing results of this interface apparatus 1 as control information. Note that the control information indicates "the determination result of the user's emotion of the interface apparatus 1", "its cause estimation result", "control contents required to remove the cause", and "control result", and is stored together with execution times of respective processes.

The information processing block 1300 is an execution block that executes respective processes to be implemented by the interface apparatus 1, and comprises a conversation analysis unit 1301, condition analysis unit 1302, cause estimation unit 1303, control information generation unit 1304, and control unit 1305.

The conversation analysis unit 1301 executes processing for analyzing the conversation contents on the basis of voice data input to this interface apparatus 1 via the voice input/output unit 1102. Since the conversation analysis processing is a state-of-the start technique, a description thereof will be omitted.

The condition analysis unit 1302 executes processing for estimating the emotion of the user 2, processing for estimating the surrounding environment of the user 2, and the like on the basis of information acquired from the sensor block 1100.

The cause estimation unit 1303 executes processing for estimating a cause of the emotion of the user 2 estimated by the condition analysis unit 1302.

The control information generation unit 1304 generates commands (control information) for executing processing contents to be executed by this interface apparatus 1 so as to remove the cause on the basis of the estimation result of the cause estimation unit 1303.

The control unit 1305 executes processing according to the commands (control information) generated by the control information generation unit 1304.

Then, the results of a series of processes done by the information processing block 1300, i.e., the emotion estimation result, cause estimation result based on the emotion estimation result, and control result based on the cause estimation result are recorded as one set in the control information storage unit 1204.

Note that only the user himself or herself can confirm details of data stored in the information storage block 1200 to protect his or her privacy, and only a determination result (e.g., something wrong has occurred or the like) is presented to other users. This presentation is made by a conversation or data transmission between the user 2 and interface apparatus 1. Data transmission can be made at a desired time and to a desired destination in accordance with settings if it is set in advance. Since the information processing block 1300 comprises person identifying unit as following description, the privacy problem can be avoided even if a person is not identified using a password or the like.

The processing to be executed by this interface apparatus 1 will be described below. The following explanation will be given under the assumption that the interface apparatus 1 is equipped in a classroom of a school for the sake of simplicity. Therefore, the measuring instruments 3 are attached to all students (including the user 2) in the classroom, and the person data storage unit 1202 stores personal data of all the students in the classroom.

Under such settings, the interface apparatus 1 executes processing for always collecting image and voice data in the classroom, and storing condition information based on image and voice data at that time and living body information already transmitted from the measuring instrument 3 at that time in the event log storage unit 1201 together with date and time data. A mode that collects the conditions in the classroom in this way is called a normal mode. Therefore, the interface apparatus 1 executes processing for collecting the conditions in the classroom in the normal mode.

Figure 2:
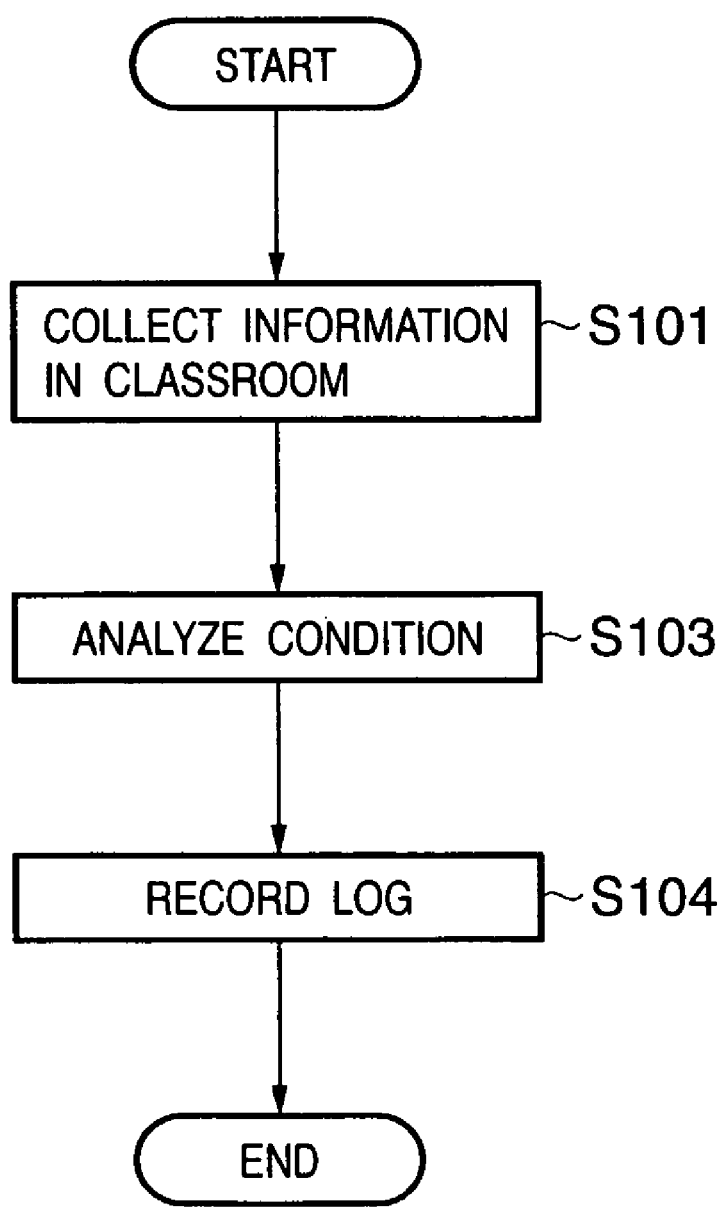
FIG. 2 is a flowchart of processing to be executed by an interface apparatus 1 in a normal mode.

FIG. 2 is a flowchart of processing to be executed by the interface apparatus 1 in the normal mode.

The interface apparatus 1 executes processing for collecting the conditions in the classroom (step S101). More specifically, the interface apparatus 1 receives image data in the classroom via the image input unit 1101 and voice data via the voice input/output unit 1102. Also, the interface apparatus 1 receives living body information of respective students periodically transmitted from the measuring instrument 3 attached to the respective students. Furthermore, the interface apparatus 1 measures the temperature, humidity, and illuminance by the thermometer 1104, hygrometer 1105, and illuminometer 1106.

Next, the condition analysis unit 1302 executes processing for estimating the conditions in the image data acquired from the image input unit 1101 (step S103). Details of the processing in step S103 will be described below.

Figure 3:
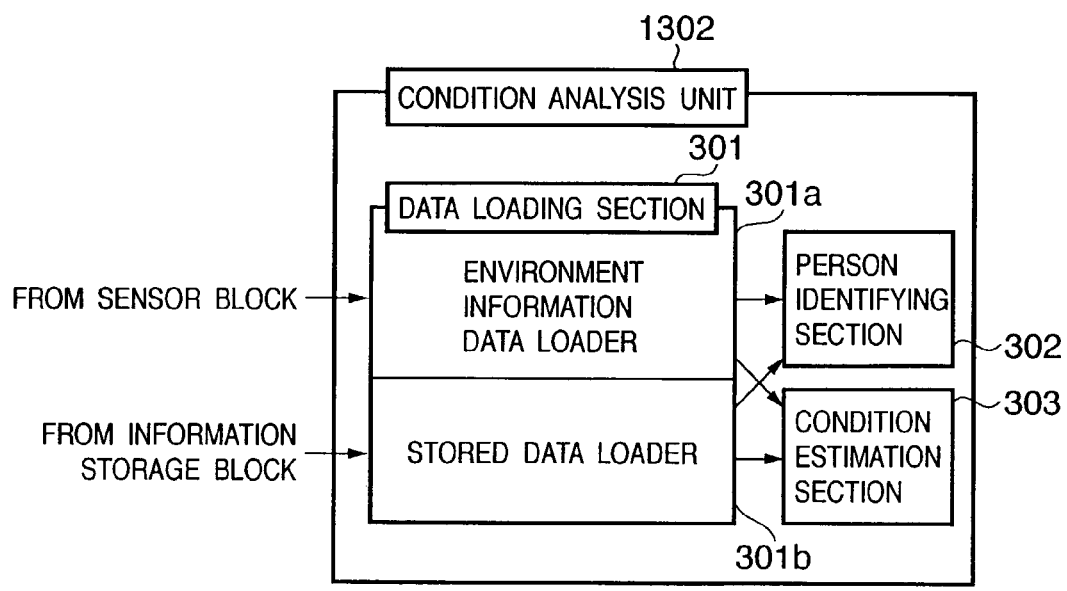
FIG. 3 is a block diagram showing the functional arrangement of a condition analysis unit 1302.

FIG. 3 is a block diagram showing the functional arrangement of the condition analysis unit 1302. The condition analysis unit 1302 comprises a data loading section 301, person identifying section 302, and condition estimation section 303. Furthermore, the data loading section 301 comprises an environment information data loader 301a and stored data loader 301b.

The environment information data loader 301a loads an information group obtained from the sensor block 1100. The stored data loader 301b loads an information group recorded in the information storage block 1200.

The person identifying section 302 specifies a student who appears in an image by collating image and voice data input from the sensor block 1100 with personal data input from the stored data loader 301b.

For example, since a face region of a person who appears in an image input from the sensor block 1100 can be specified by a known technique, the face image in this face region is compared with those of respective students (included in personal data of the respective students) to identify the face in this face region. Since the technique for identifying the face that appears in an image in this way is known to those who are skilled in the art, a detailed description thereof will be omitted.

A feature amount is extracted from the voice signal input from the sensor block 1100 by a known technique, and the extracted feature amount is compared to those of voice data of the respective students (included in personal data of the respective students) to identify the voice signal input from the sensor block 1100. Since the technique for identifying the voice of the collected voice signal in this way is known to those who are skilled in the art, a detailed description thereof will be omitted.

In this manner, an individual who appears in the image is identified.

The condition estimation section 303 estimates the emotion of the individual identified by the person identifying section 302 on the basis of the information group input from the sensor block 1100. That is, the condition estimation section 303 analyzes the image and voice data of the individual input from the sensor block 1100 to make emotion recognition, i.e., if this individual is laughing or angry. For example, if the eyes are slanting down outwards, the mouth is open widely, the voice is loud and the frequency characteristic has a high level in the high-frequency range, and the action is brisk, it is determined that the individual is "cheerful". Since the technique for making emotion recognition of the individual using image and voice data in this way is a state-of-the-art technique, a description thereof will be omitted.

In some cases, the identified individuals may be in the middle of a conversation. In such case, action recognition of each individual must be made.

With this processing, a person who appears in the image can be identified, and the emotion of the identified person can be estimated.

Referring back to FIG. 2, processing for recording the analysis result of the condition estimation section 303 in the event log storage unit 1201 as a log is executed (step S104). Upon recording the analysis result as a log, a recording date and time are additionally recorded. The date and time are measured by the control unit 1305.

A log to be recorded has contents, for example, "O/O, O:O, A and B had a cheerful conversation". Also, for example, upon recording such log, it is determined based on the log contents "A", "B", and "cheerful" that A and B are in good terms, and data that advises accordingly is recorded together with the log.

In this manner, the emotion of each student who appears in the image obtained from the image input unit 1101 and the conditions in the classroom can be estimated.

The interaction mode as a mode in which this interface apparatus 1 has a conversation with the user 2 will be described below. Note that this interaction mode indicates a mode for a contact between the user 2 and this interface apparatus 1, e.g., a dialogue, communication, or the like. Switching to the interaction mode can be attained by operating a switch or the like (not shown). Hence, processing is normally done in the normal mode, and when a conversation is to be made using this interface apparatus 1, the control transits to the interaction mode by operating a switch or the like. Note that the means and method for making transition to the interaction mode are not limited to this.

At this time, since this interface apparatus 1 has a conversation with the user 2, the image input unit 1101 captures an image including the user 2, and the voice input/output unit 1102 collects voice data from the user 2 (of course, voice data other than that of the user 2 is also collected).

Figure 4A:
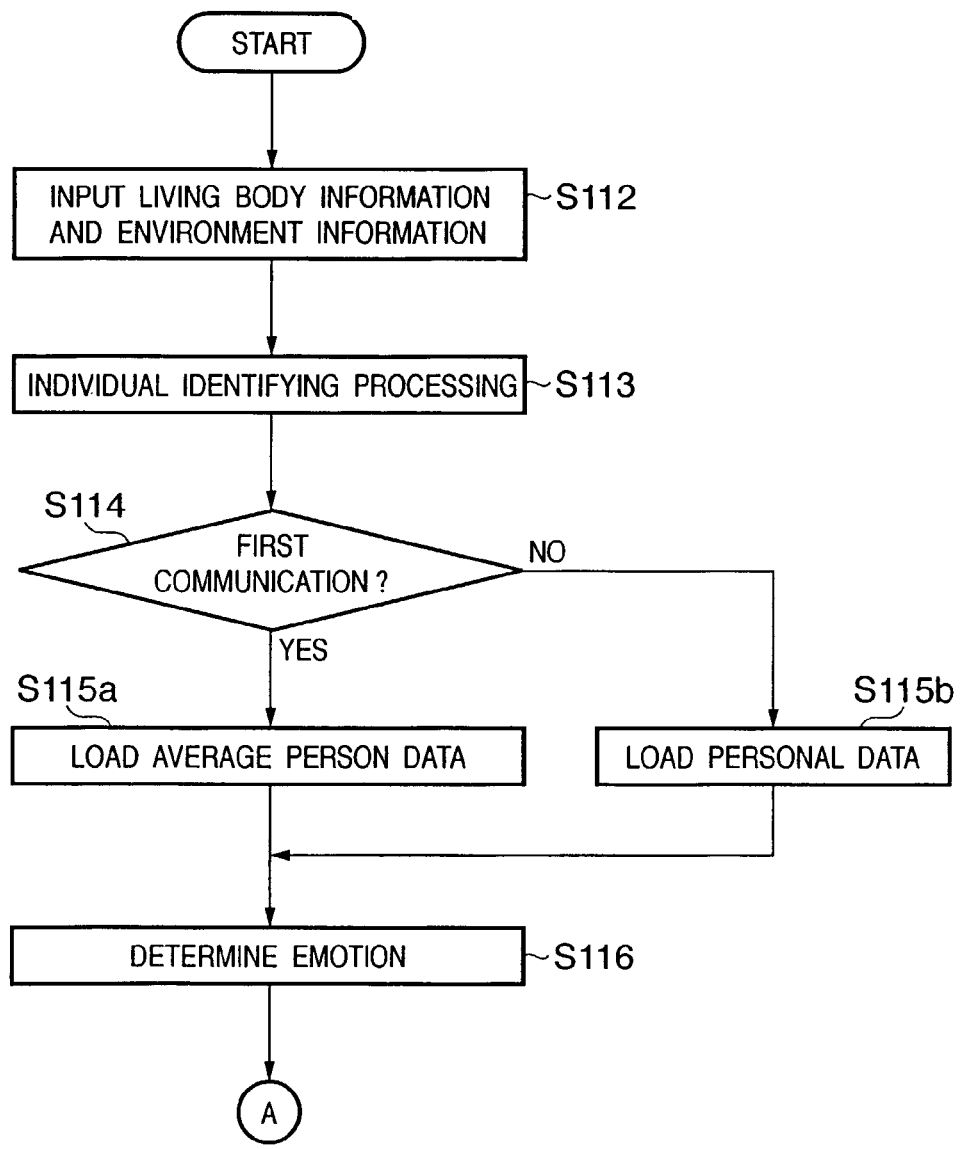
FIG. 4A is a flowchart of processing to be executed by the interface apparatus 1 in an interaction mode.
Figure 4B:
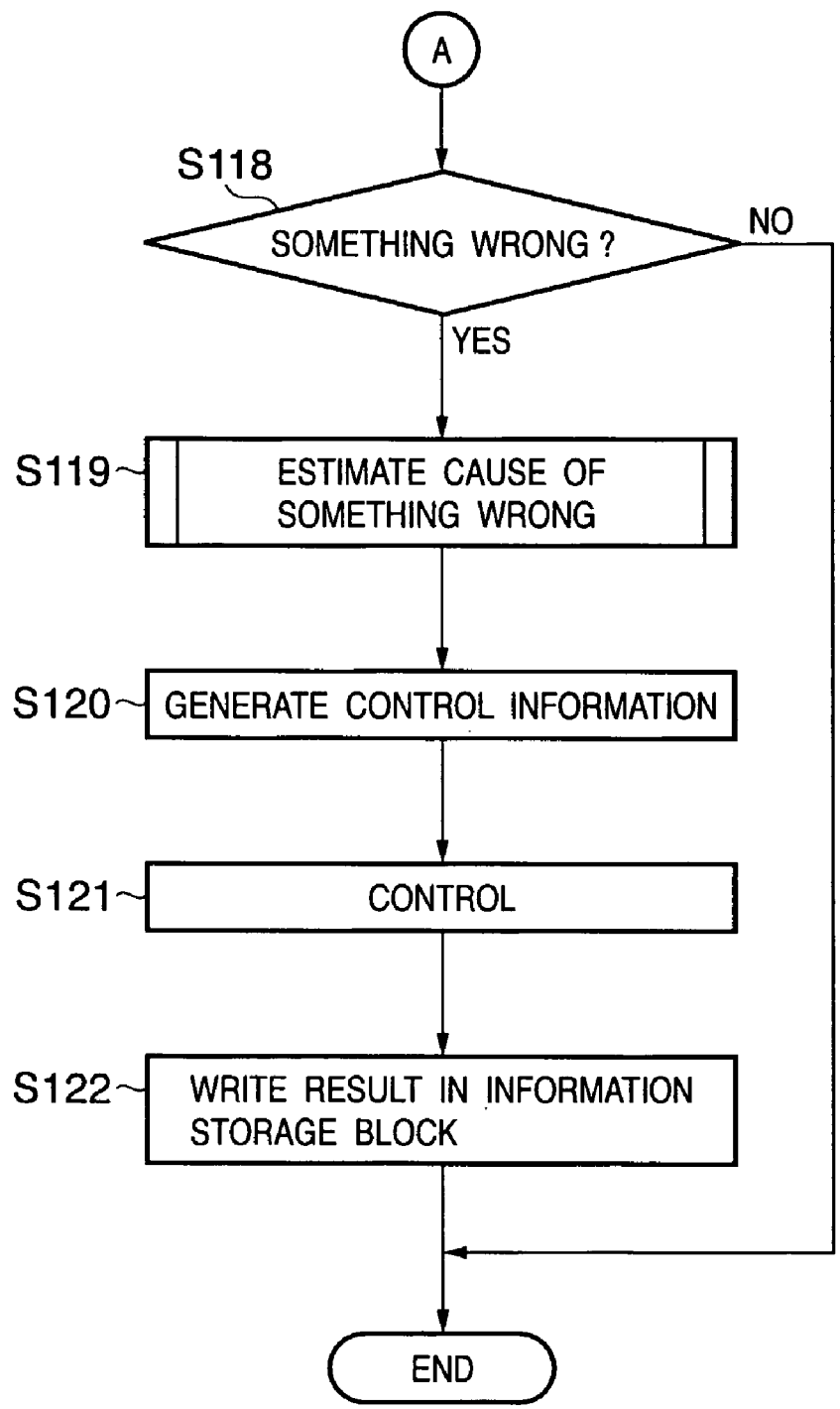
FIG. 4B is a flowchart of processing to be executed by the interface apparatus 1 in the interaction mode.

FIGS. 4A and 4B are flowcharts of processing to be executed by the interface apparatus 1 in the interaction mode.

The interface apparatus 1 executes processing for collecting the conditions in the classroom (step S112). More specifically, the interface apparatus 1 receives image data in the classroom via the image input unit 1101 and voice data via the voice input/output unit 1102. Also, the interface apparatus 1 receives living body information of respective students periodically transmitted from the measuring instrument 3 attached to the respective students. Furthermore, the interface apparatus 1 measures the temperature, humidity, and illuminance, in the classroom, by the thermometer 1104, hygrometer 1105, and illuminometer 1106.

Next, the interface apparatus 1 executes the person identifying processing in image data which is executed in step S103, and also the processing for recording information indicating the identified person in the event log storage unit 1201 (step S113). The control unit 1305 checks if the apparatus previously communicated with the person identified in step S113 (step S114). This processing is done by checking if "information indicating persons with whom the apparatus previously communicated" recorded in the event log storage unit 1201 includes information indicating the currently identified person.

As a result, if no information indicating the currently identified person is recorded in the event log storage unit 1201 as a log (if the apparatus communicates with the currently identified person for the first time), the flow advances to step S115a, and the condition analysis unit 1302 reads out average person data stored in the average person data storage unit 1203 (step S115a). On the other hand, if the information indicating the currently identified person is recorded in the event log storage unit 1201 as a log (if the apparatus previously communicated with the currently identified person), the flow advances to step S115b, and the condition analysis unit 1302 reads out personal data of the currently identified person from the person data storage unit 1202 (step S115b).

The condition analysis unit 1302 executes the processing for estimating the emotion of the person in the image, which is executed in step S103, using the image information, voice information, living body information, and environment information obtained in step S112 and average person data obtained in step S115a or personal data obtained in 115b (step S116). In this case, the emotion of the user 2, which is determined from the image obtained from the image input unit 1101, is estimated.

However, although one's psychological state is directly linked with emotions in many cases, emotions may sometimes appear while internally masking a real psychological state, and this mode aims at finding it out. For example, even when the emotion estimated from the image is "cheerful, happily", if the pulse rate is high, the body temperature is relatively low, and the frequency characteristic of the voice is unnaturally high in the high-frequency range, the psychological state of the person is estimated that he or she may be forcing a laugh. In this manner, when the emotion is to be estimated using a plurality of pieces of information, an emotion estimated based on given referred information may be opposite to that estimated using another information.

Hence, in this embodiment, if an emotion estimated from the image data, that estimated from the voice data, and that estimated from the living body information include at least one negative emotion (down, sad, or the like), it is determined that "something wrong has occurred" (step S118), and the flow advances to step S119. On the other hand, if emotions are estimated using respective pieces of information, and they indicate roughly equal emotions independently of information used, this processing ends.

Furthermore, a change in psychological state can be checked by comparing the current data of the user 2 with his or her old data. For example, even if the user 2 replies "Good", if it is determined as a result of expression analysis that the reply is in low spirits since the eyes look hollow, the voice is soft, the frequency characteristic has a high level in the low-frequency range, and so forth, or if a feature indicating that a sweating amount is larger than an ordinary one is extracted from the image information or living body information, the condition estimation section 303 estimates that "The user appears depressed. That may be a trouble that he (or she) cannot talk to others", and also estimates that "something wrong has occurred in the psychological state".

In case of "something wrong has occurred", the cause estimation unit 1303 executes processing for estimating a cause that drives to the negative emotion estimated in step S116 (step S119). For example, if the plurality of emotions estimated for the user 2 by the condition analysis unit 1302 include an estimation result "down", the cause estimation unit 1303 estimates its cause.

Figure 5:
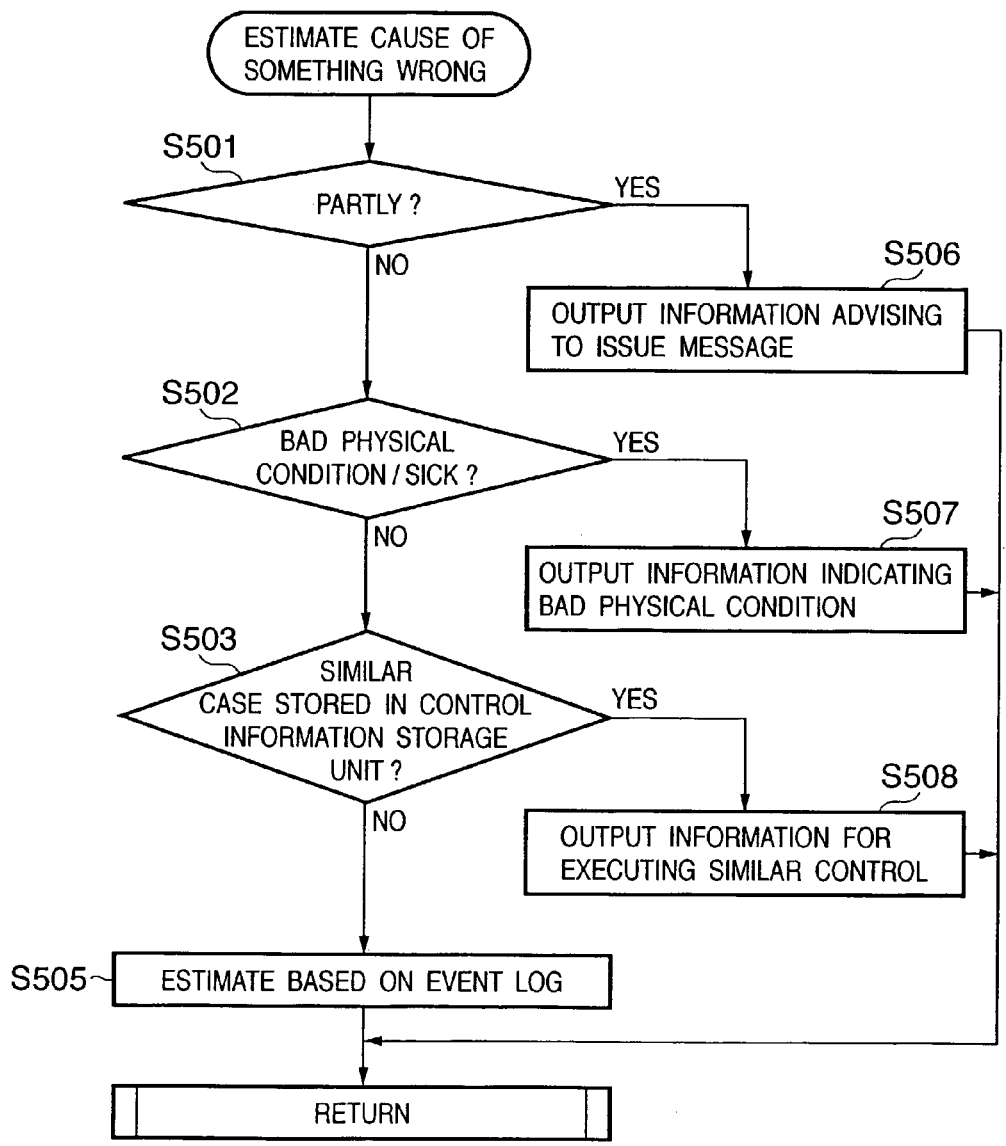
FIG. 5 is a flowchart showing details of processing in step S119.

FIG. 5 is a flowchart showing details of the processing in step S119. If only one of the emotion estimated from the image data, that estimated from the voice data, and that estimated from the living body information is a negative emotion (step S501), the flow advances to step S506, and the cause estimation unit 1303 determines that a message for the purpose of caring about this negative emotion (e.g., a message "Are you OK?" or the like) is to be output to the voice input/output unit 1102, and outputs information that advises accordingly to the control information generation unit 1304 (step S506).

On the other hand, if two or more of the emotion estimated from the image data, that estimated from the voice data, and that estimated from the living body information include negative emotions (step S501), the flow advances to step S502 to check the physical condition of the user 2 with reference to the living body information input in step S112 (step S502). More, specifically, the physical condition of the user 2 is checked by comparing the average body temperature and average pulse rate included in the personal data of the user 2 stored in the person data storage unit 1202 with the body temperature and pulse rate included in the living body information input in step S112. Note that the cause estimation unit 1303 holds in advance as data whether the physical condition is good/bad depending on the relationship between the body temperature and pulse rate, and average ones.

As a result of checking, if the current body temperature of the user 2 is largely different from the average body temperature (i.e., the user is running a fever), and the pulse rate is largely different from the average pulse rate (i.e., the pulse rate is not stable), it is determined that the physical condition of the user 2 is bad (step S502), and the flow advances to step S507. In step S507, it is determined that a message informing the bad physical condition is to be output, and information that advises accordingly is output to the control information generation unit 1304 (step S507).

On the other hand, if the current body temperature of the user 2 is nearly the same as the average body temperature (i.e., the user is not running a fever), and the pulse rate is nearly the same as the average pulse rate (i.e., the pulse rate is stable), it is determined that the physical condition of the user 2 is good, and the flow advances to step S503. In step S503, information associated with previous control for similar emotions is searched for with reference to information associated with the user 2 of those held by the control information storage unit 1204 (step S503). If the information associated with previous control for similar emotions is found, the flow advances to step S508, and the found information is output to the control information generation unit 1304 (step S508).

On the other hand, if no information associated with previous control for similar emotions is found, the flow advances to step S505, and all logs associated with the user 2 of those held by the event log storage unit 1201 are extracted to estimate a cause (step S505). When a log "O/O, O:O, A and B had a cheerful conversation" of old logs associated with the user 2 is recorded together with a log "A and B are in good terms", but a recent log "x/x, x:x, A and B have a quarrel" is recorded together with a log "A and B are at strife", it is estimated that A is depressed owing to this quarrel.

In this manner, when the logs associated with the user 2 are referred to, and a log (second log) indicating a condition opposite to that indicated by the referred log (first log) is recorded later, the condition recorded in the second log is estimated as a cause.

In this manner, the cause of the current emotion of the user 2 can be estimated. Note that the cause estimation method is not limited to this, and various other methods may be used. For example, logs which are associated with the user 2 and are recorded in the event log storage unit 1201 during a predetermined period of time before the time at which the estimated emotion changed, and the condition indicated by logs in a group with a largest number of logs of those which indicate similar conditions may be estimated as a cause. That is, various other methods may be used.

Upon completion of the processing according to the flowchart shown in FIG. 5, the flow returns to step S120 in FIG. 4B, and the control information generation unit 1304 generates a command (control information) which makes the control unit 1305 execute processing to be executed on the basis of the information received from the condition analysis unit 1302 (step S120).

For example, since the information indicating that a message for the purpose of caring about this negative emotion (e.g., a message "Are you OK?" or the like) is to be output to the voice input/output unit 1102 is input to the control information generation unit 1304 in step S506, the control information generation unit 1304 generates a command for making the control unit 1305 issue such message, and outputs that command to the control unit 1305.

Since the information indicating that a message informing the bad physical condition is to be output is input to the control information generation unit 1304 in step S507, the control information generation unit 1304 generates a command for making the control unit 1305 execute processing for outputting a message informing the bad physical condition, and outputs that command to the control unit 1305.

Since the information found in step S503 is input to the control information generation unit 1304 in step S508, the control information generation unit 1304 generates a command for making the control unit 1305 execute control processing according to this information, and outputs that command to the control unit 1305.

Hence, the control unit 1305 executes processing according to the command received from the control information generation unit 1304 (step S121).

For example, upon reception of the command required to output a message for the purpose of caring about this negative emotion (e.g., a message "Are you OK?" or the like) to the voice input/output unit 1102, the control unit 1305 reads out message data according to this command from its internal memory, and outputs it to the voice input/output unit 1102. The voice input/output unit 1102 generates a voice according to this message data by a speech synthesis technique or the like, and outputs the voice.

Upon reception of the command required to execute processing for outputting a message informing the bad physical condition, the control unit 1305 reads out message data for informing the bad physical condition of the user 2 (e.g., "the physical condition of the user 2 is bad") from its internal memory, and outputs it to the voice input/output unit 1102. The voice input/output unit 1102 generates a voice according to this message data by a speech synthesis technique or the like, and outputs the voice.

Upon reception of the information found in step S503, the control unit 1305 executes control for previous similar emotions.

The control unit 1305 records the contents of a series of the processes, i.e., data for identifying the individual (the user 2 in this case) identified in step S113, the interaction contents for this individual, the emotion estimation result for this individual in step S116, and the cause estimation result of this emotion in step S119, in the control information storage unit 1204 as a log of the current processing (step S122). This recorded log is referred to when it is searched in step S503 for previous information indicating persons and their emotions, and control processing executed depending on causes.

The information storage block 1200 has performance that stores all pieces of environment information, conversation contents, and the like, but informs persons other than the authenticated user himself or herself of only the condition analysis result and control information and protects individual privacy such as the living body information and conversation contents. For example, assume that the user 2 asks the interface apparatus 1 "O looked depressed O/O, and what were you talking about?". However, when the user 2 is determined by the person identifying section 302 as a person other than the user himself or herself, the apparatus limits disclosure of information to "O was depressed O/O. But he (or she) became cheerful after conversation for about 30 minutes", and does not disclose any conversation contents. By providing the privacy protection function, the user can express true feelings with a sense of security.

In this embodiment, the means for informing the user 2 of a message uses a voice. However, a display device may be newly added to this interface apparatus 1, and a message may be displayed on the display device as a text message. The informing method is not particularly limited.

Second Embodiment

This embodiment uses the interface apparatus in use application different from the first embodiment.

Figure 6:
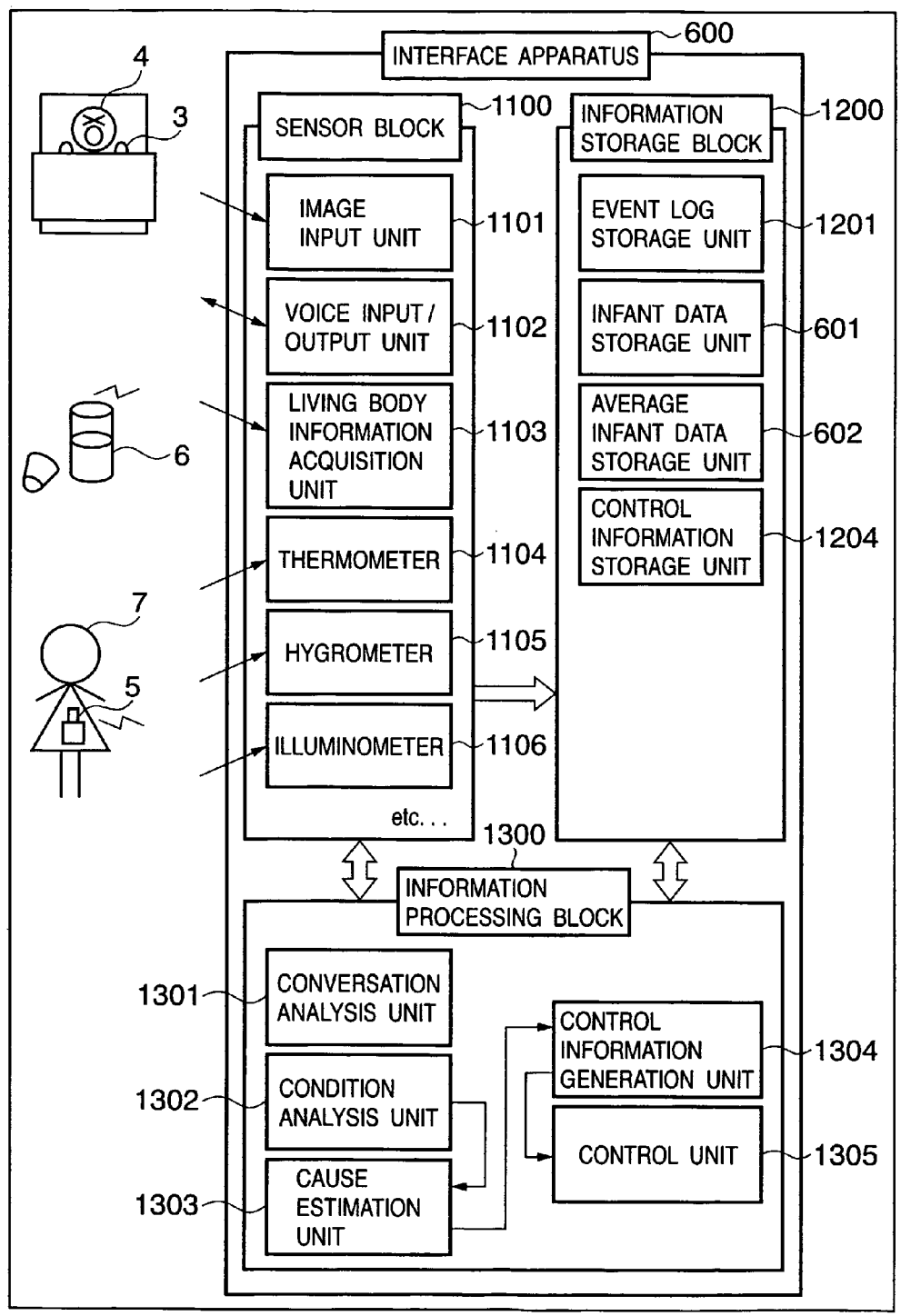
FIG. 6 is a block diagram showing the functional arrangement of a system including an interface apparatus according to the second embodiment of the present invention.

FIG. 6 is a block diagram showing the functional arrangement of a system including an interface apparatus according to this embodiment. In the following description, assume that units which form an interface apparatus 600 shown in FIG. 6 are configured by hardware components. However, some or all of these units may be implemented by software. Also, the same reference numerals in FIG. 6 denote the same parts as in FIG. 1, and a description thereof will be omitted.

Referring to FIG. 6, reference numeral 4 denotes an infant as a person to be aided. In the following description, the interface apparatus 600 assists child-care help for this infant 4. The same measuring instruments 3 as in the first embodiment is attached to this infant 4, and living body information about this infant 4 is periodically transmitted to the interface apparatus 600 by radio.

Reference numeral 7 denotes a person who cares for this infant 4 (e.g., the mother of the infant 4). The caretaker 7 always carries a data receiver 5 which receives data transmitted from the interface apparatus 600, and visually/audibly outputs the received data. In this embodiment, the control unit 1305 has an external communication function, i.e., a data transmission function to this data receiver 5.

Reference numeral 6 denotes a feeding bottle with a sensor. This feeding bottle 6 has a sensor which measures a quantity of milk currently stored in this feeding bottle, and periodically transmits the measured quantity to the interface apparatus 600. Note that this sensor is not particularly limited, and it may be a sensor that measures any quantity as long as it can specify the quantity of milk such as the volume, weight, or the like.

The differences of the interface apparatus 600 from the interface apparatus 1 of the first embodiment are that an infant data storage unit 601 that stores data associated with the infant 4 is equipped in place of the person data storage unit 1202, and an average infant data storage unit 602 is equipped in place of the average person data storage unit 1203.

Figure 7A:
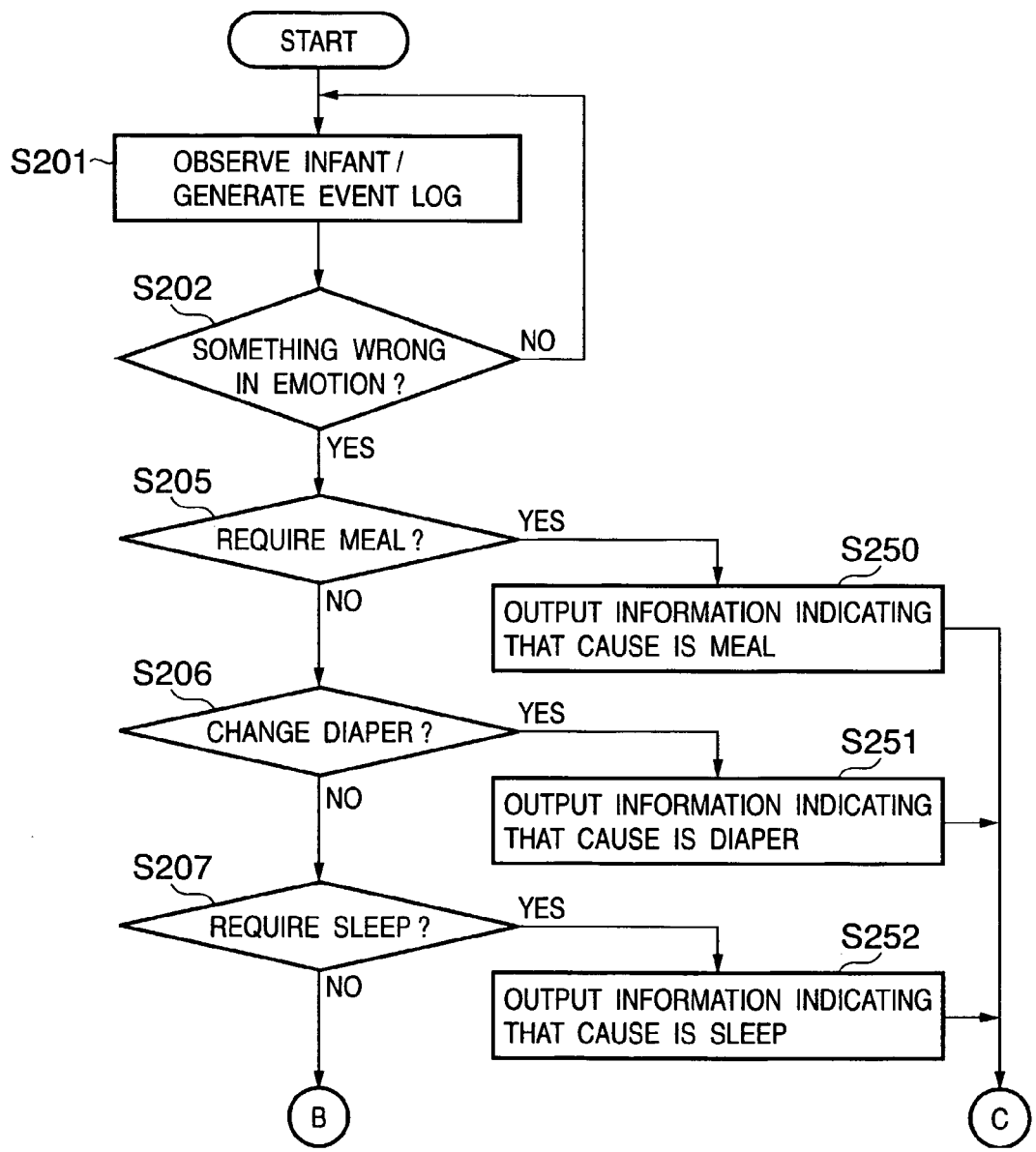
FIG. 7A is a flowchart of processing to be executed by an interface apparatus 600 according to the second embodiment of the present invention.
Figure 7B:
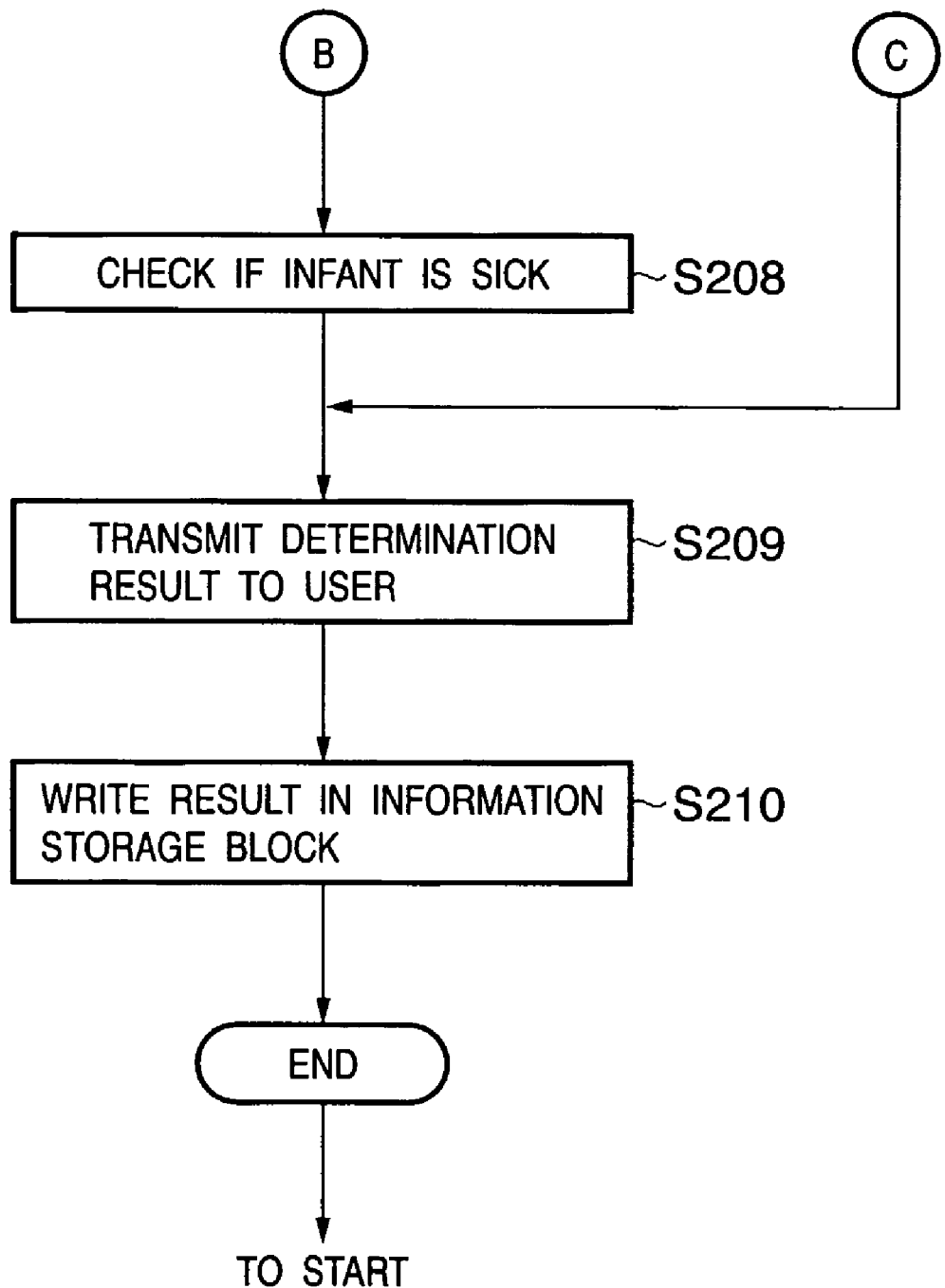
FIG. 7B is a flowchart of processing to be executed by the interface apparatus 600 according to the second embodiment of the present invention.

FIGS. 7A and 7B are flowcharts of processing to be executed by the interface apparatus 600 according to this embodiment.

The image input unit 1101 inputs an image of a surrounding environment including the infant 4, the voice input/output unit 1102 inputs a voice of the infant 4, the living body information acquisition unit 1103 inputs living body information including the body temperature, pulse rate, and the like of the infant 4 transmitted from the measuring instrument 3, and the feeding bottle 6 with a sensor inputs the quantity of milk. Hence, these data are stored in the event log storage unit 1201 as a log together with recording date and time data (step S201).

Upon recording this log, the condition analysis unit 1302 recognizes with reference to the image from the image input unit 1101 whether or not the infant 4 is eating, whether or not he or she is crying, whether or not a diaper is being changed, and the like, and records the recognition result (infant state) together with this log (step S202). In order to recognize the condition in an image such as the action, gesture, and the like of a person in the image, a technique for recognizing the condition in a given image using a neural network that has learned images under various conditions may be used. However, the present invention is not limited to such specific technique.

When this recognition result is "something is wrong with the infant 4", e.g., "the infant 4 is crying" in this embodiment, the flow advances to step S205. In order to precisely recognize that the infant is crying, the voice information obtained from the voice input/output unit 1102 may also be referred to. As for a technique for recognizing based on the voice information whether or not this voice is a crying voice, a technique for recognizing whether a given voice is a crying or laughing voice using a neural network that has learned voices under various conditions may be used. However, the present invention is not limited to such specific technique.

When it is recognized that the infant 4 is crying, the cause estimation unit 1303 executes processing for estimating a cause of crying.

The cause estimation unit 1303 checks with reference to the log recorded in the event log storage unit 1201 if a meal is required (step S205). More specifically, the cause estimation unit 1303 specifies a start time of the meal with reference to the log. Then, the cause estimation unit 1303 specifies the quantity of milk at the specified time. Next, the cause estimation unit 1303 specifies an end time of the meal and also the quantity of milk at the specified time. Then, the cause estimation unit 1303 can calculate the quantity of the previous meal by calculating the difference between the specified quantities of milk.

On the other hand, since data which is associated with this infant 4 and stored in the infant data storage unit 601 includes data indicating the quantity of a single meal, the cause estimation unit 1303 checks if the calculated quantity of the previous meal is equal to or smaller than that of the single meal indicated by this data.

If the calculated quantity of the previous meal is equal to or smaller than that of the single meal indicated by this data, the cause estimation unit 1303 estimates that the infant is crying since he or she is hungry.

Note that the method of checking if the infant is hungry is not limited to this. The following method may be used. That is, a possibility indicating if the current time is a meal time is calculated by:

Possibility of meal time=(previous meal quantity/ elapsed time from previous meal)/(average meal quantity/meal interval)

The "previous meal quantity" is calculated as described above. As for the "elapsed time from previous meal", since the end time of the meal can be specified from the log, and the current time is measured, the difference between these times can be calculated as the elapsed time. The "average meal quantity" and "meal interval" are obtained from the previous logs of the meal quantity and meal time of the infant 4.

As a calculation result of the above equation, if the possibility is equal to or lower than 1.2, it is determined that the current time is the meal time.

As a result of the above processing, if the cause of crying is a meal, the flow advances to step S250, and the cause estimation unit 1303 outputs information advising that the cause of crying is a meal to the control information generation unit 1304 (step S250).

On the other hand, if the cause of crying is not a meal, the flow advances to step S206 to check if the cause of crying is a diaper (step S206). The cause estimation unit 1303 specifies the last time the diaper was changed with reference to the log recorded in the event log storage unit 1201. The cause estimation unit 1303 calculates the difference between the specified time and current time, and checks if the difference is equal to or larger than a predetermined value, i.e., if a time has sufficiently elapsed from the previous diaper change time. As this predetermined value, the average value of diaper change time intervals is used. However, the present invention is not limited to this.

Note that the method of estimating whether or not the cause is a diaper is not limited to this.

If the cause of crying is a diaper, the flow advances to step S251, and the cause estimation unit 1303 outputs information advising that the cause of crying is a diaper to the control information generation unit 1304 (step S251).

On the other hand, if the cause of crying is not a diaper, the flow advances to step S207 to check if the cause of crying is lack of sleep (step S207). The previous sleeping time is calculated by calculating the difference between the last falling-asleep time and the wake-up time with reference to the log recorded in the event log storage unit 1201. It is then checked if the calculated sleeping time is equal to or shorter than a predetermined value, i.e., if the previous sleeping time is not sufficient. As this predetermined value, the average value of the intervals of the sleeping start and end times recorded in old logs is used. However, the present invention is not limited to such specific value.

Note that the method of estimating whether or not the cause is lack of sleep is not limited to this.

If the cause of crying is lack of sleep, the flow advances to step S252, and the cause estimation unit 1303 outputs information advising that the cause of crying is lack of sleep to the control information generation unit 1304 (step S252).

On the other hand, if the cause of crying is not lack of sleep, the flow advances to step S208 to check the physical condition of the infant 4 with reference to the living body information input in step S201 (step S208). More specifically, the physical condition of the infant 4 is checked by comparing the average body temperature and average pulse rate included in the personal data of the infant 4 stored in the infant data storage unit 601, and the body temperature and pulse rate included in the living body information input in step S201. Note that the cause estimation unit 1303 holds in advance as data whether the physical condition is good/bad depending on the relationship between the body temperature and pulse rate, and average ones.

As a result of checking, if the current body temperature of the infant 4 is largely different from the average body temperature (i.e., the infant is running a fever), and the pulse rate is largely different from the average pulse rate (i.e., the pulse rate is not stable), it is determined that the physical condition of the infant 4 is bad and a message informing the bad physical condition is to be output, and information that advises accordingly is output to the control information generation unit 1304 (step S208).

Next, the control information generation unit 1304 generates a command (control information) which makes the control unit 1305 execute processing to be executed on the basis of the information received from the condition analysis unit 1302, and transmits the generated command to the control unit 1305. Then, the control unit 1305 executes processing according to this command (step S209).

For example, since information indicating that the cause of crying is a meal is input to the control information generation unit 1304 in step S250, the control information generation unit 1304 generates a command for making the control unit 1305 execute processing for transmitting a message "give the infant 4 a meal" to the data receiver 5, and outputs the command to the control unit 1305.

Since information indicating that the cause of crying is a diaper is input to the control information generation unit 1304 in step S251, the control information generation unit 1304 generates a command for making the control unit 1305 execute processing for transmitting a message "change a diaper" to the data receiver 5, and outputs the command to the control unit 1305.

Since information indicating that the cause of crying is lack of sleep is input to the control information generation unit 1304 in step S252, the control information generation unit 1304 generates a command for making the control unit 1305 execute processing for transmitting data of a lullaby to the data receiver 5, and outputs the command to the control unit 1305.

Since information indicating that the cause of crying is the bad physical condition of the infant 4 is input to the control information generation unit 1304 in step S208, the control information generation unit 1304 generates a command for making the control unit 1305 execute processing for transmitting a message "the physical condition of the infant 4 is bad" to the data receiver 5, and outputs the command to the control unit 1305.

Hence, the control unit 1305 executes processing according to the command received from the control information generation unit 1304.

For example, upon reception of the command for making the control unit 1305 execute processing for transmitting a message "give the infant 4 a meal" to the data receiver 5, the control unit 1305 reads out message data according to this command from its internal memory, and transmits it to the data receiver 5. As a result, the data receiver 5 generates a voice according to this message data by a speech synthesis technique or the like, and outputs the voice.

Upon reception of the command for making the control unit 1305 execute processing for transmitting a message "change a diaper" to the data receiver 5, the control unit 1305 reads out message data according to this command from its internal memory, and transmits it to the data receiver 5. As a result, the data receiver 5 generates a voice according to this message data by a speech synthesis technique or the like, and outputs the voice.

Upon reception of the command for making the control unit 1305 execute processing for transmitting data of a lullaby to the data receiver 5, the control unit 1305 reads out its own data of the lullaby, and transmits it to the data receiver 5. As a result, the data receiver 5 plays back and outputs this data of the lullaby.

Upon reception of the command for making the control unit 1305 execute processing for transmitting a message "the physical condition of the infant 4 is bad" to the data receiver 5, the control unit 1305 reads out message data according to this command from its internal memory, and transmits it to the data receiver 5. As a result, the data receiver 5 generates a voice according to this message data by a speech synthesis technique or the like, and outputs the voice.

In this manner, the caretaker 7 who holds the data receiver 5 can be informed of the state of the infant 4.

The control unit 1305 executes processing for recording information corresponding to that used as the previous log in the processing of those used in a series of processes in the event log storage unit 1201 (step S210).

Third Embodiment

This embodiment uses the interface apparatus in a use application different from the first and second embodiments.

Figure 8:
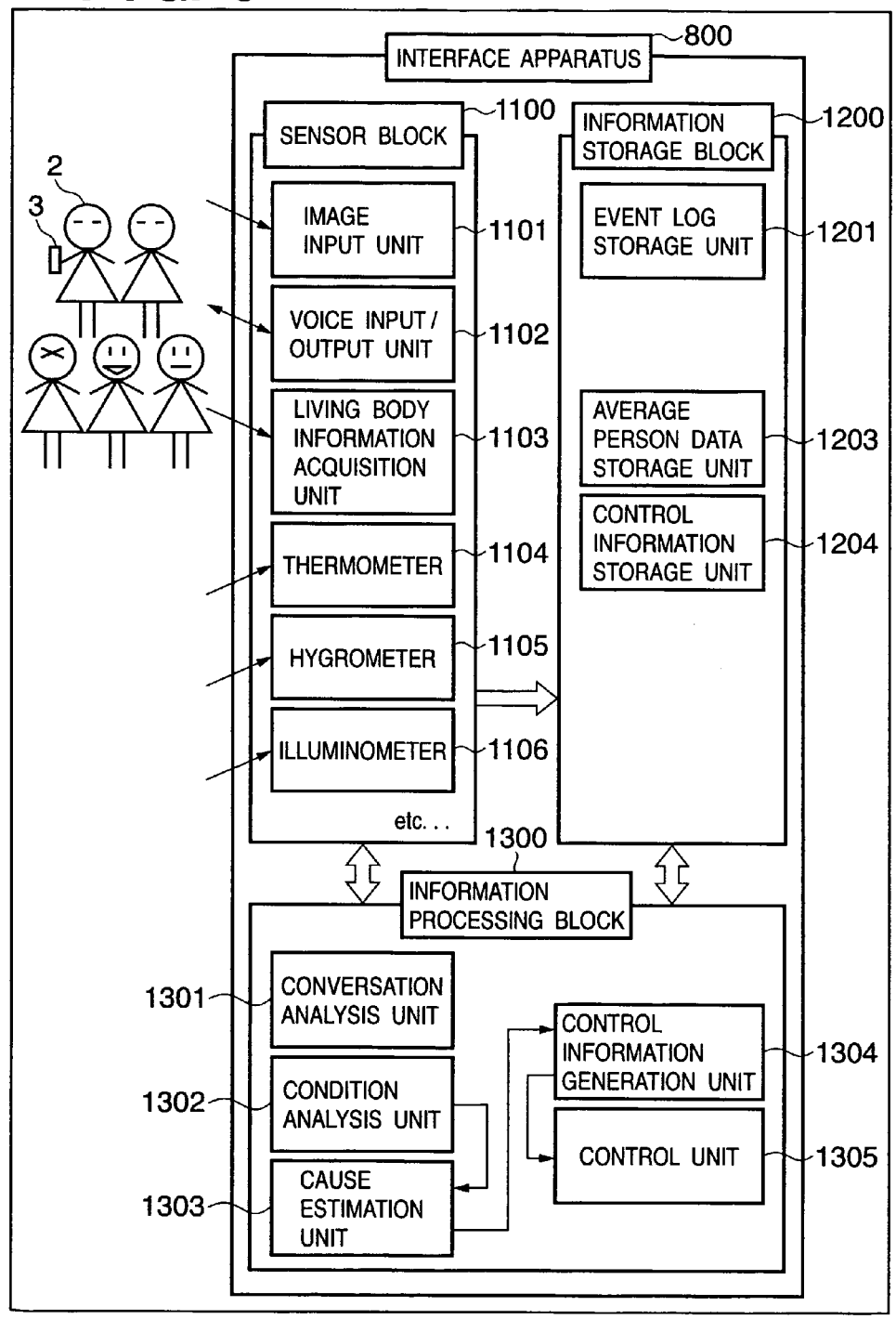
FIG. 8 is a block diagram showing the functional arrangement of a system including an interface apparatus according to the third embodiment of the present invention.

FIG. 8 is a block diagram showing the functional arrangement of a system including an interface apparatus according to this embodiment. In the following description, assume that units which form an interface apparatus 800 shown in FIG. 8 are configured by hardware components. However, some or all of these units may be implemented by software. Also, the same reference numerals in FIG. 8 denote the same parts as in FIG. 1, and a description thereof will be omitted.

Referring to FIG. 8, reference numeral 2 denotes a user indoors. In the following description, the interface apparatus 800 assists all the members including the user 2 to spend the time comfortably indoors. Note that "indoor" means an air-conditioned space, and the same applies to the following description if this space is an interior of a train, vehicle, or the like.

Figure 9A:
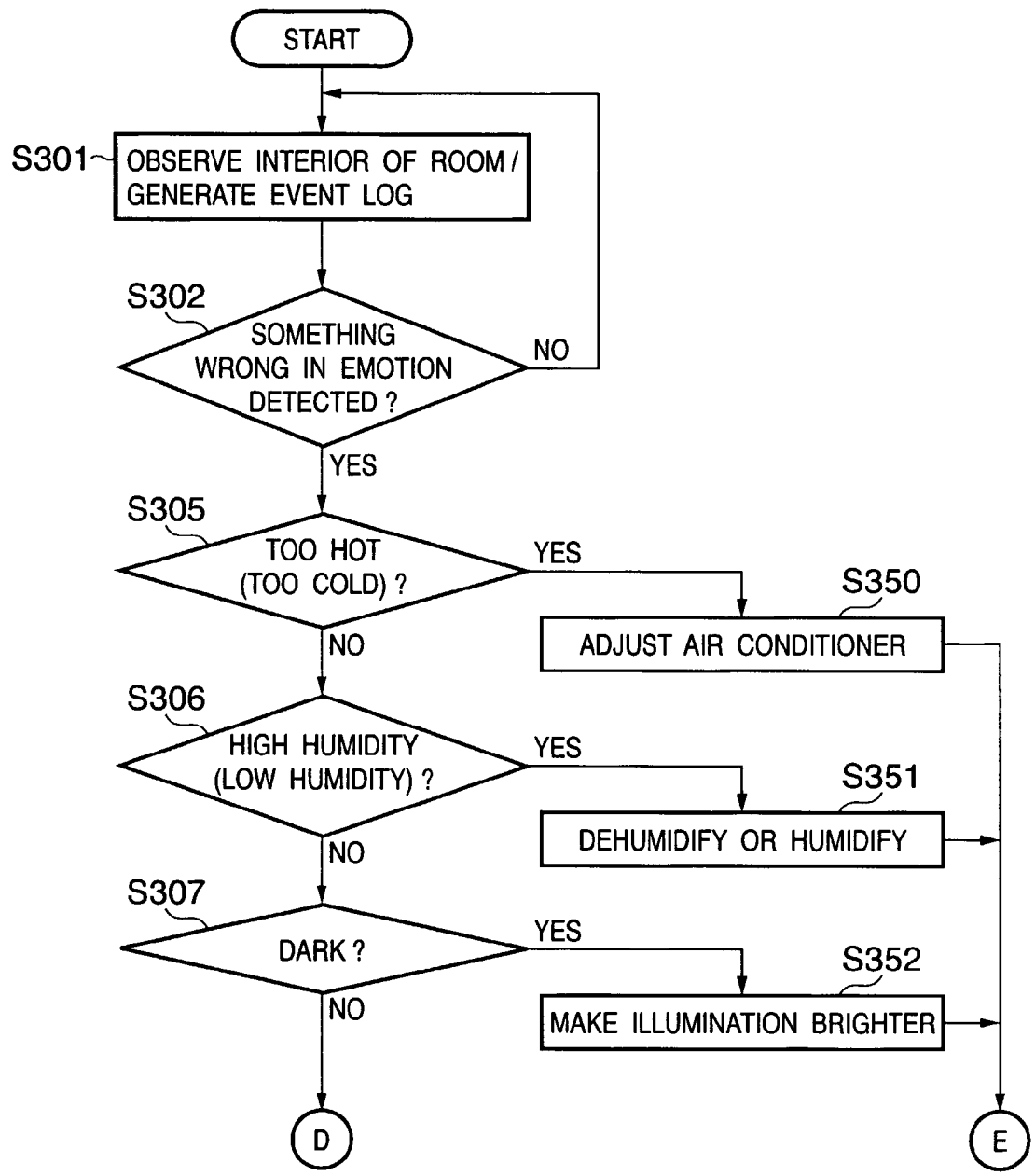
FIG. 9A is a flowchart of processing to be executed by an interface apparatus 800 according to the third embodiment of the present invention.
Figure 9B:
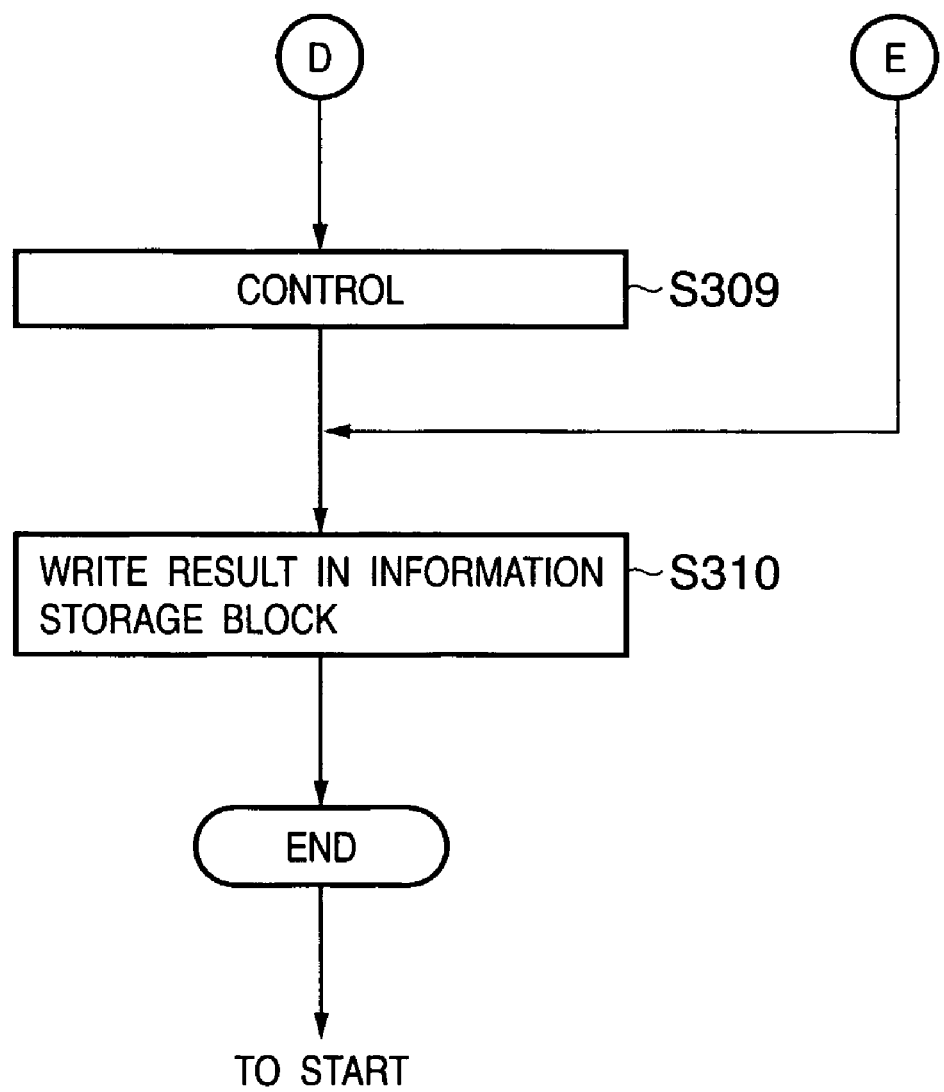
FIG. 9B is a flowchart of processing to be executed by the interface apparatus 800 according to the third embodiment of the present invention.

FIGS. 9A and 9B are flowcharts of processing to be executed by the interface apparatus 800 according to this embodiment.

The image input unit 1101 inputs an image of a surrounding environment including the user 2, the voice input/output unit 1102 inputs a voice of the user 2, the living body information acquisition unit 1103 inputs living body information such as body temperature, pulse count and the like of the user 2 transmitted from the measuring instrument 3. The indoor temperature, humidity, and illuminance are input from the thermometer 1104, hygrometer 1105, and illuminometer 1106. Hence, these data are stored in the event log storage unit 1201 as a log together with recording date and time data (step S301).

Upon recording this log, the condition analysis unit 1302 recognizes with reference to the image from the image input unit 1101 whether the user 2 feels hot or cold, whether the interior of the room is bright or dark, and so forth, and records the recognition result together with this log (step S302).

For example, if sweat on the forehead of the user 2 is recognized from the image input from the image input unit 1101, and the temperature input from the thermometer 1104 is 27° C. or higher, it is recognized that "the user 2 feels hot". The action of the user 2 is recognized, and if the recognition result is an arm-rubbing action, and the temperature input from the thermometer 1104 is 25° C. or lower, it is recognized that "the user 2 feels cold". In this manner, the emotion of the user 2 is estimated using information input from the sensor block 1100.

As for indoor conditions, when the humidity input from the hygrometer 1105 exceeds, e.g., 80%, it is recognized that "the humidity is high". Also, when the illuminance input from the illuminometer 1106 is equal to or lower than a predetermined value, it is determined that "the interior of the room is dark".

In order to recognize the condition in an image such as the action, gesture, and the like of a person in the image, a technique for recognizing the condition in a given image using a neural network that has learned images under various conditions may be used. However, the present invention is not limited to such specific technique.

If this recognition result indicates that "something is wrong with the user 2", i.e., if one of "the user feels hot (cold)", "the humidity is high (low)", and "the interior of the room is dark" is the analysis result of the condition analysis unit 1302, the condition analysis unit 1302 determines that "something is wrong with the user 2".

The aforementioned processing is applied to persons other than the user 2 in the image input from the image input unit 1101, and if it is determined that "something is wrong with more than half of all persons in the image", the flow advances to step S305.

The cause estimation unit 1303 executes processing for estimating a cause of something wrong of respective persons in the room.

The cause estimation unit 1303 checks with reference to the log recorded in the event log storage unit 1201 in step S301 previously if the cause of something wrong is "the user 2 (or a user other than the user 2; the user 2 as the representative in this case) feels hot or cold" (step S305). As a result, if "the user 2 feels hot or cold", the flow advances to step S350. In step S350, information that advises to decrease the room temperature by adjusting an air conditioner if the user 2 feels hot, or to increase the room temperature by adjusting the air conditioner if the user 2 feels cold is output to the control information generation unit 1304 (step S350).

On the other hand, if the cause of something wrong is not "the user 2 feels hot or cold", the flow advances to step S306, and the cause estimation unit 1303 checks with reference to the log recorded in the event log storage unit 1201 in step S301 previously if the cause of something wrong is "the humidity is high or low" (step S306). As a result, if "the humidity is high or low", the flow advances to step S351. In step S351, information that advises to dehumidify by adjusting the air conditioner if the humidity is high, or to humidify by adjusting the air conditioner if the humidity is low is output to the control information generation unit 1304 (step S351).

On the other hand, if the cause of something wrong is not the humidity, the flow advances to step S307, and the cause estimation unit 1303 checks with reference to the log recorded in the event log storage unit 1201 in step S301 previously if the cause of something wrong is "the interior of the room is dark" (step S307). As a result, if "the interior of the room is dark", the flow advances to step S352, and information that advises to make the interior of the room brighter by adjusting an illumination is output to the control information generation unit 1304 (step S352).

Next, the control information generation unit 1304 generates a command (control information) which makes the control unit 1305 execute processing to be executed on the basis of the information received from the condition analysis unit 1302, and transmits the generated command to the control unit 1305. Then, the control unit 1305 executes processing according to this command (step S309).

For example, since the information that advises to increase/decrease the room temperature by adjusting the air conditioner is input to the control information generation unit 1304 in step S350, the control information generation unit 1304 generates a command for making the control unit 1305 issue a message "increase/decrease the room temperature", and outputs the message to the control unit 1305.

Since the information that advises to dehumidify/humidify by adjusting the air conditioner is input to the control information generation unit 1304 in step S351, the control information generation unit 1304 generates a command for making the control unit 1305 issue a message "dehumidify/humidify", and outputs the message to the control unit 1305.

Since the information that advises to make the interior of the room brighter is input to the control information generation unit 1304 in step S351, the control information generation unit 1304 generates a command for making the control unit 1305 issue a message "make the interior of the room brighter", and outputs the message to the control unit 1305.

Hence, the control unit 1305 executes processing according to the command received from the control information generation unit 1304.

For example, upon reception of the command required to issue the message "increase/decrease the room temperature", the control unit 1305 reads out data of this message from its internal memory, and outputs it to the voice input/output unit 1102. The voice input/output unit 1102 generates a voice according to this message data by a speech synthesis technique or the like, and outputs the voice.

Upon reception of the command required to issue the message "increase/decrease the room humidity", the control unit 1305 reads out data of this message from its internal memory, and outputs it to the voice input/output unit 1102. The voice input/output unit 1102 generates a voice according to this message data by a speech synthesis technique or the like, and outputs the voice.

Upon reception of the command required to issue the message "make the interior of the room brighter", the control unit 1305 reads out data of this message from its internal memory, and outputs it to the voice input/output unit 1102. The voice input/output unit 1102 generates a voice according to this message data by a speech synthesis technique or the like, and outputs the voice.

In this way, the interior of the room can be maintained comfortable. Note that the control unit 1305 may directly control the temperature or humidity in place of issuing the aforementioned messages.

The control unit 1305 executes processing for recording information corresponding to that used as the previous log in the processing of those used in a series of processes in the event log storage unit 1201 (step S310).

Fourth Embodiment

The interface apparatus according to each of the above embodiments may be built in, e.g., a personal computer, monitoring camera, or the like as a single built-in device.

Other Embodiments

The objects of the present invention are also achieved when a CPU or MPU of a computer reads out and executes a program code from a recording medium (or storage medium), which records a program code of a software program that can implement the functions of the above-mentioned embodiments. In this case, the program code itself read out from the recording medium implements the functions of the above-mentioned embodiments, and the recording medium which stores the program code constitutes the present invention.

The functions of the above-mentioned embodiments may be implemented not only by executing the readout program code by the computer, but also by some or all of actual processing operations executed by an operating system (OS) running on the camera on the basis of an instruction of the program code.

Furthermore, the functions of the above-mentioned embodiments may be implemented by some or all of actual processing operations executed by a CPU or the like arranged in a function extension card or a function extension unit, which is inserted in or connected to the computer, after the program code read out from the recording medium is written in a memory of the extension card or unit.

When the present invention is applied to the recording medium, that recording medium stores program codes corresponding to the aforementioned flowchart (functional arrangement).

As many apparently widely different embodiments of the present invention can be made without departing from the spirit and scope thereof, it is to be understood that the invention is not limited to the specific embodiments thereof except as defined in the claims.

CLAIM OF PRIORITY

This application claims priority from Japanese Patent Application No. 2004-312858 filed on Oct. 27, 2004, which is hereby incorporated by reference herein.

The invention claimed is:

1. An estimation apparatus comprising:
image input means for inputting image data of a user;
voice input means for inputting voice data of the user;
living body information input means for inputting living body information of the user;
an event log recording means for recording an event log including a time at which a remedial action was taken by a person other than the user;
first estimation means for estimating a surrounding environment of the user on the basis of the image data, voice data, and living body information;
holding means for holding reference data serving as a reference used upon estimating a psychological state of the user;
second estimation means for estimating the psychological state of the user by comparing at least one of the image data, voice data, and living body information with the reference data;
calculation means for calculating an elapsed time from the last time in the event log at which the remedial action was taken by a person other than the user;
third estimation means for, when the psychological state of the user estimated by the second estimation means is a predetermined psychological state, estimating a cause of the predetermined psychological state of the user on the basis of the surrounding environment estimated by the first estimation means and the elapsed time calculated by the calculation means; and
instruction means for instructing a person other than the user to perform a remedial action for removing the cause of the predetermined psychological state of the user estimated by the third estimation means.

2. The apparatus according to claim 1, wherein the predetermined psychological state is a state in which at least one of an emotion estimated by the second estimation means based on the image data, an emotion estimated by the second estimation means based on the voice data, and an emotion estimated by the second estimation means based on the living body information are negative emotions.

3. The apparatus according to claim 1, further comprising informing means for informing a result estimated by the third estimation means.

4. The apparatus according to claim 1, further comprising fourth estimation means for, when the psychological state of the user estimated by the second estimation means is the predetermined psychological state, estimating based on the living body information whether or not a physical condition of the user is bad.

5. The apparatus according to claim 4, further comprising informing means for informing a result estimated by the fourth estimation means.

6. A control method comprising:
using a central processing unit programmed to perform:
an image input step of inputting image data of a user;
a voice input step of inputting voice data of the user;
a living body information input step of inputting living body information of the user;
an event log recording step of recording an event log including a time at which a remedial action was taken by a person other than the user;
a first estimation step of estimating a surrounding environment of the user on the basis of the image data, voice data, and living body information;
a holding step of holding reference data serving as a reference used upon estimating a psychological state of the user;
a second estimation step of estimating the psychological state of the user by comparing at least one of the image data, voice data, and living body information with the reference data;
a calculation step of calculating an elapsed time from the last time in the event log at which the remedial action was taken by a person other than the user;
a third estimation step of estimating, when the psychological state of the user estimated in the second estimation step is a predetermined psychological state, a cause of the predetermined psychological state of the user on the basis of the surrounding environment estimated in the first estimation step and the elapsed time calculated in the calculation step; and an instruction step of instructing a person other than the user to perform a remedial action for removing the cause of the predetermined psychological state of the user estimated in the third estimation step.

7. A computer program stored in a non-transitory computer-readable storage medium to make a computer execute the control method of claim 6.

* * * * *